United States Patent [19]

Muszak et al.

[11] Patent Number: 5,106,586

[45] Date of Patent: Apr. 21, 1992

[54] J-SHAPED SPRING USED IN INCUBATOR

[75] Inventors: Martin F. Muszak, Rochester; James D. Shaw, Hilton, both of N.Y.

[73] Assignee: Eastman Kodak Company, Rochester, N.Y.

[21] Appl. No.: 527,501

[22] Filed: May 23, 1990

[51] Int. Cl.$^5$ .................... G01N 21/00; B01L 11/00; F16F 1/18

[52] U.S. Cl. ........................................ 422/99; 422/64; 267/158

[58] Field of Search ................. 422/99, 64, 104, 68.1; 436/46; 267/158, 159, 163

[56] References Cited

U.S. PATENT DOCUMENTS

| | | |
|---|---|---|
| 2,805,297 | 9/1957 | Campbell .................... 267/159 |
| 4,431,876 | 2/1984 | Labude et al. ................ 200/5 R |
| 4,467,085 | 8/1984 | Scharf ........................... 536/43 |
| 4,505,010 | 3/1985 | Arenhold ...................... 267/158 |
| 4,814,279 | 3/1989 | Sugaya ......................... 422/104 |
| 4,935,374 | 6/1990 | Jacobs et al. ................. 422/99 |
| 4,943,415 | 7/1990 | Przybylowicz et al. ....... 422/64 |

*Primary Examiner*—Robert J. Warden
*Assistant Examiner*—Theresa A. Trembley
*Attorney, Agent, or Firm*—Dana M. Schmidt

[57] ABSTRACT

There are disclosed a spring and its combination with an evaporation cover for a test element, and a station of an incubator. The spring comprises two portions bent to form the letter "J". The longer portion includes means for retaining the spring in the incubator station, and the shorter portion includes means for retaining a cover under the spring.

6 Claims, 2 Drawing Sheets

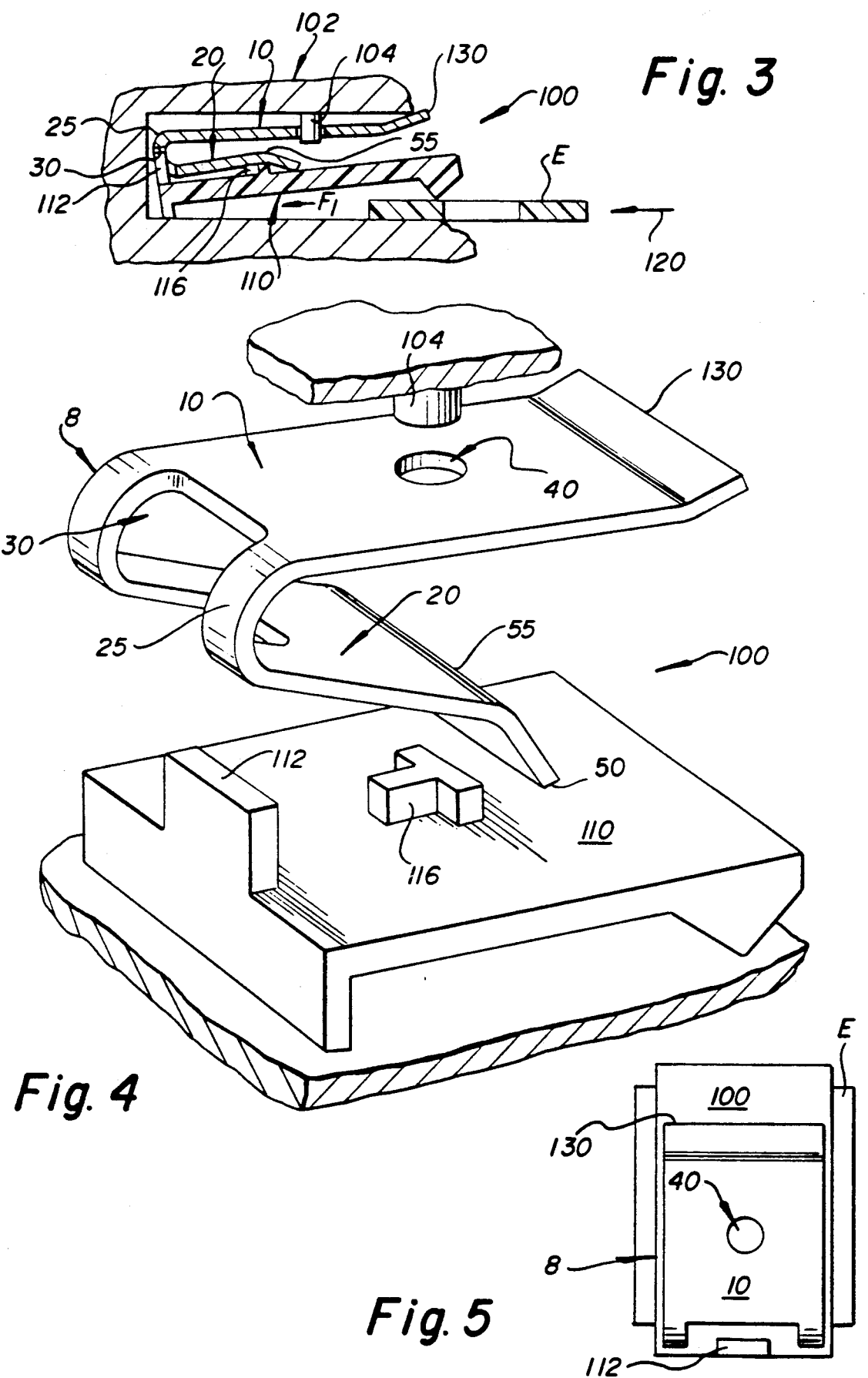

J-SHAPED SPRING USED IN INCUBATOR

FIELD OF THE INVENTION

The invention concerns a spring and particularly a spring used in an incubator station to hold down an evaporation cover onto a test element.

BACKGROUND OF THE INVENTION

In conventional incubators for analyzers, evaporation covers are provided to hold test elements at the stations of the incubator. Such covers are spring-biased downwardly, to allow the test elements to be inserted and removed against the bias of the spring.

Although this arrangement has worked satisfactorily, there have been some disadvantages with the springs heretofore provided. In some cases, the springs comprise a simple one-leg leaf element screwed into place to bias the cover downwardly. Such springs are not readily removable, for example, in case of a jam or if cleaning is needed. In other cases, removable leaf springs have been provided, but such springs have been fairly complicated in shape. For example, as shown in commonly-owned U.S. application Ser. No. 346,205 filed on May 2, 1989 and entitled "Universal Evaporation Cover", now U.S. Pat. No. 4,963,333, there is disclosed a spring having three legs projecting from a body. Although such a spring works satisfactorily in most instances, it has a disadvantage in that its shape is more complicated, and thus more difficult to manufacture and assemble. Furthermore, its design features an aperture in the longest of the three legs to retain the evaporation cover with respect to the spring. Such an aperture necessarily involves a sloppy fit, that tends to render uncertain the exact location of the cover in the station of the incubator. For best operation of the cover, it is preferred that the cover always be fully withdrawn into the station of the incubator. This did not always occur using such an aperture.

Therefore, there has been a need prior to this invention to provide a spring for covers in an incubator that avoids the above-noted disadvantages.

SUMMARY OF THE INVENTION

We have constructed a spring that solves the above-noted problems.

More particularly there is provided, in accord with one aspect of the invention, a leaf spring for holding a cover on a test element at a station in an analyzer, the spring having only a first and a second portion, the second portion extending from the first portion along a bend line that forms an approximate 150° angle, the first portion having a lateral extension from the bend line that exceeds the corresponding lateral extension of the second portion, so that the spring is in the shape of a "J" when viewed from the side, and further including retaining means in both the first portion and second portion for retaining the spring in relation to an analyzer, and for biasing a cover into the station.

In accord with another aspect of the invention, there is provided a leaf spring for holding a cover on a test element at a station in an analyzer, the spring comprising a first and a second portion, the second portion extending from the first portion along a bend line that forms an approximate 150° angle, the first portion having a lateral extension from the bend line that exceeds the corresponding lateral extension of the second portion, so that the spring is in the shape of a "J" when viewed from the side, and further including retaining means in both the first portion and second portion for retaining the spring in relation to an analyzer, and for biasing a cover into the station, the retaining means comprising a first aperture in at least the first portion, and a second aperture in the bend line, and a bend adjacent the edge of the second portion farthest from the bend line, the bend being at an angle that moves the farthest edge away from the first portion.

In accord with yet another aspect of the invention, there is provided, in combination, a station of an incubator, an evaporation cover for a test element at the station, and a spring holding the cover in the station, the spring having the features set forth in either of the two previous paragraphs.

Accordingly, it is an advantageous feature of the invention that a spring is provided for covers in an incubator that is both simple in construction and provides more positive inward biasing of the cover.

Other advantageous features will become apparent upon reference to the following Description of the Preferred Embodiments, when read in light of the attached drawings.

BRIEF DESCRIPTION OF THE DRAWINGS

FIG. 3 is a fragmentary elevational view in section of an incubator station assembled with the spring of the invention, the section being taken through the approximate center of the station;

FIG. 4 is a fragmentary exploded perspective view of the station of FIG. 3, but without element E; and FIG. 5 is a plan view of the spring as it sits on a cover on a test element.

DESCRIPTION OF THE PREFERRED EMBODIMENTS

The invention is hereinafter described with respect to a preferred incubator station and preferred covers, for use with preferred test elements. In addition, it is useful regardless of the type of incubator, cover, or test element that is being used, provided the cover needs to be biased in the incubator to cover the test element. Also, the relative dimensions are not critical, except where stated.

Figure 1:
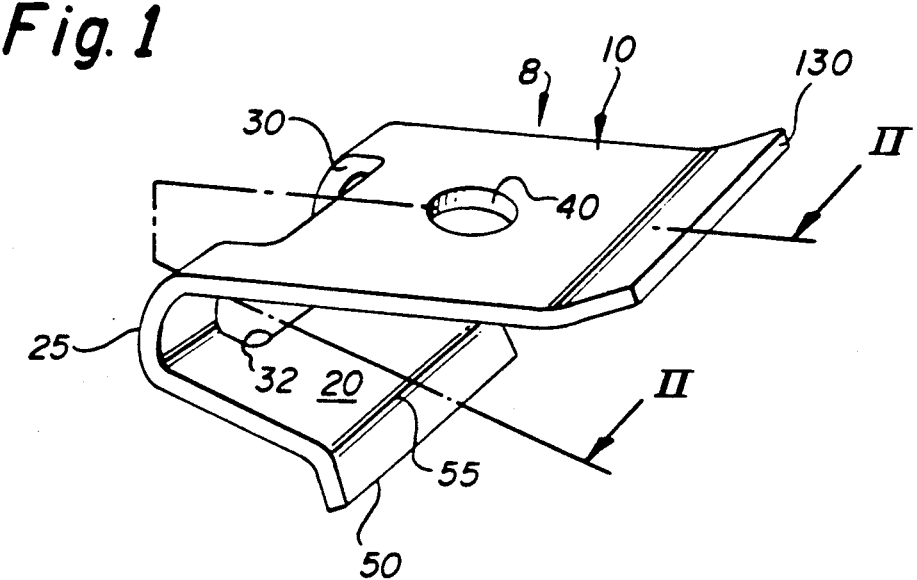
FIG. 1 is a perspective view of the spring of the invention.

As shown in FIG. 1, spring 8 has two portions, a first portion 10 and a second portion 20, which together when viewed from the side (or in cross-section, FIG. 2) provide the shape of a "J". That is, portion 10 is substantially longer than portion 20. For example, portion 10 can be 3.5 cm long, and portion 20 1.5 cm long. Other lengths are also useful. Portion 20 is bent about a bend line 25 such that it forms a bending angle alpha of approximately 150°, FIG. 2. This angle can be varied by ±10°, depending upon the amount of bias that needs to be applied to the cover underneath it, described hereinafter. Bend line 25 is itself not a sharp intersection, but rather a relatively blunt one.

To retain portion 10 and hence the entire spring in the incubator station, an aperture 40 is formed in portion 10. Its dimensions are selected to closely mate with those of a post fixed to the station. The size and shape, therefore, of aperture 40 depends on that of the post. A circular post and aperture are preferred.

Figure 2:
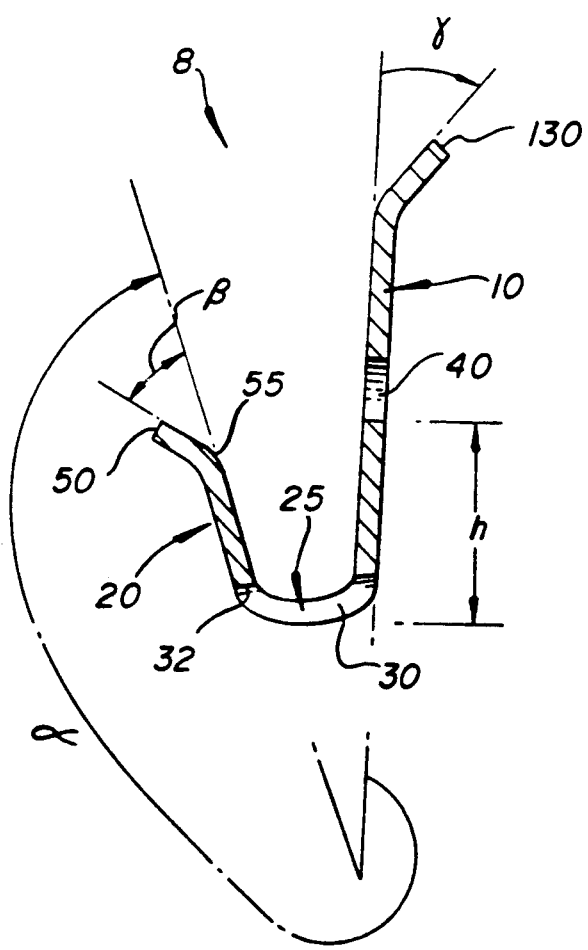
FIG. 2 is a section view taken generally along the plane II—II of FIG. 1.

Portion 10 has an end 130 that optionally extends out of the plane of the rest of portion 10 by an angle gamma, FIG. 2, that can be any angle from 0° to about 45°C. This angle makes grasping of the spring, when mounting the analyzer, somewhat easier.

To retain a cover underneath spring 8, retaining means are provided in portion 20. Such means preferably include an aperture 30 formed within bend line 25, sized to receive a shoulder projecting from the cover, described hereinafter. Aperture 30 extends into portion 20 sufficiently to provide an edge 32, FIG. 1, against which the cover shoulder is retained in the presence of forces trying to pull cover 110 out of station 100, FIG. 3. Alternatively, edge 32 can be formed only in the bend line 25 and not extend into portion 20 (not shown).

The retaining means of portion 20 also preferably include a bend 55 formed adjacent to extreme end 50 of portion 20 that is opposite to bend line 25. Bend 55 is formed to project end 50 further away from the plane of portion 10, than is the rest of portion 20. The amount of the bend forms an angle beta, FIG. 2, which is selected to be that amount which provides adequate retention of a post 116 approximately centered in the top of a cover, described below. Beta is a value preferably between about 20 and about 40 degrees.

Spring 8 is used in combination with a station 100, FIG. 3, of incubator 102 and a cover 110 for a test element E. Portion 10 slips over and clips onto a post 104 of station 100, while portion 20 retains cover 110. Cover 110 has an upwardly projecting shoulder 112 at the rear portion 114 of the cover, which slips into and is held by aperture 30 at bend line 25. A post 116 of the cover engages bend 55 of portion 20, such bend being effective to bias cover 110 backward with a force $F_1$. The entire spring then acts to bias cover 110 downwardly, with a force that will still allow a test element E to be inserted, arrow 120.

Cover 110 need only be wide enough to cover spot S of element E that has been wetted. It may cover almost the entire element E, FIG. 5, but in any event it sits on top of element E instead of surrounding it.

Any shape can be given to post 116. Most preferably, it has a T-shape, FIG. 4, to best mate with bend 55 to cause the rearward bias of cover 110.

Because of the relative locations of post 104 and post 116 in station 100, distance "h" from aperture 40 to bend line 25 exceeds the length of spring portion 20, FIG. 2.

The preferred relative sizes of spring 8 and cover 110 are shown in FIG. 5. Other relative sizes are also useful.

Both the spring and the cover are readily removed simply by pinching end 130 of portion 10, FIG. 3, towards cover 110, and removing them both.

The invention has been described in detail with particular reference to preferred embodiments thereof, but it will be understood that variations and modifications can be effected within the spirit and scope of the invention.

What is claimed is:

1. A leaf spring for holding a cover on a test element at a station in an analyzer, said spring comprising only a first and a second portion, the second portion extending from said first portion along a bend line that forms an approximate 150° angle, said first portion having an extension from said bend line that exceeds a corresponding extension of said second portion, so that the spring is in the shape of a "J" when viewed from the side, and further including retaining means in both said first portion and second portion for retaining said spring in relation to an analyzer, and for biasing a cover into said station, said retaining means including in at least one of said portions, a bend at an edge farthest away from said bend line, said bend in said edge extending away from said other portion.

2. A spring as defined in claim 1, wherein said retaining means comprise an aperture in said first portion sized to receive a post projecting from the analyzer.

3. A spring as defined in claim 1, wherein said retaining means comprise an aperture in said bend line sized to receive a shoulder of a cover for a test element.

4. A leaf spring for holding a cover on a test element at a station in an analyzer, said spring comprising a first and a second portion, said second portion extending from said first portion along a bend line that forms an approximate 150° angle, said first portion having an extension from said bend line that exceeds a corresponding extension of said second portion, so that the spring is in the shape of a "J" when viewed from the side, and further including retaining means in both said first portion and second portion for retaining said spring in relation to an analyzer, and for biasing a cover into said station, said retaining means comprising first and second apertures, said first aperture being in at least said first portion, said second aperture being in said bend line, and a bend adjacent the edge of said second portion farthest from said bend line, said bend being at an angle that moves said farthest edge away from said first portion.

5. In combination, a station of an incubator, and evaporation cover for a test element at said station, and a spring pushing under compression said cover in said station away from a fixed surface, towards a test element in said station, said spring comprising only a first portion and a second portion, said second portion extending from said first portion along a bend line that forms an approximate 150° angle, said first portion having an extension from said bend line that exceeds the corresponding extension of said second portion, so that the spring is in the shape of a "J" when viewed from the side, and further including retaining means in both said first portion and second portion for retaining said spring in relation to an analyzer, and for biasing a cover into said station.

6. In combination, a station of an incubator, an evaporation cover for a test element at said station, and a spring holding said cover in said station, said spring comprising a first and a second portion, said second portion extending from said first portion along a bend line that forms an approximate 150° angle, said first portion having an extension from said bend line that exceeds the corresponding extension of said second portion, so that the spring is in the shape of a "J" when viewed from the side, and further including retaining means in both said first portion and second portion for retaining said spring in relation to an analyzer, and for biasing a cover into said station, said retaining means comprising a first aperture in at least said first portion, a second aperture in said bend line, and a bend adjacent the edge of said second portion farthest from said bend line, said bend being at an angle that moves said farthest edge away from said first portion.

* * * * *